(12) United States Patent
Lenna et al.

(10) Patent No.: US 9,394,334 B2
(45) Date of Patent: Jul. 19, 2016

(54) PROCESS FOR THE PREPARATION OF DROSPIRENONE

(71) Applicant: INDUSTRIALE CHIMICA S.r.l., Milan (IT)

(72) Inventors: Roberto Lenna, Giorgio Su Legnano (IT); Andrea Vanossi, Merone (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 108 days.

(21) Appl. No.: 14/359,334

(22) PCT Filed: Nov. 21, 2012

(86) PCT No.: PCT/EP2012/073181
§ 371 (c)(1),
(2) Date: May 20, 2014

(87) PCT Pub. No.: WO2013/076118
PCT Pub. Date: May 30, 2013

(65) Prior Publication Data
US 2014/0343275 A1    Nov. 20, 2014

Related U.S. Application Data

(60) Provisional application No. 61/562,626, filed on Nov. 22, 2011.

(30) Foreign Application Priority Data

Nov. 22, 2011   (EP) .................................... 11190133
Feb. 3, 2012    (IT) ............................... MI2012A0146

(51) Int. Cl.
*C07J 53/00*   (2006.01)
*C07J 75/00*   (2006.01)

(52) U.S. Cl.
CPC .................................... *C07J 53/008* (2013.01)

(58) Field of Classification Search
CPC ........................................................ C07J 53/00
USPC .......................................................... 540/15
See application file for complete search history.

(56) References Cited

U.S. PATENT DOCUMENTS

| 6,933,395 B1 | 8/2005 | Mohr et al. |
| 7,585,971 B2 | 9/2009 | Costantino et al. |
| 2007/0021603 A1 | 1/2007 | Seilz |

FOREIGN PATENT DOCUMENTS

| EP | 1828222 A1 | 9/2007 |
| SI | 918791 T1 | 12/2002 |
| WO | 2010/118023 A1 | 10/2010 |

OTHER PUBLICATIONS

Tetrahedron Letters, vol. 27, No. 45, 1986. (Summary).
International Search Report for PCT/EP2012/073181 mailed on Jul. 2, 2013.

*Primary Examiner* — Brenda Coleman
(74) *Attorney, Agent, or Firm* — Abelman, Frayne & Schwab

(57) ABSTRACT

It is described of a process for the preparation of drospirenone, the compound of formula 1 shown below, a synthetic steroid with progestogenic, antimineralocorticoid and antiandrogenic activity, useful for preparing pharmaceutical compositions having contraceptive action, starting from 17α-(3-hydroxypropyl)-6β,7β;15β,16β-dimethylene-5β-androstane-3β,5,17β-triol.

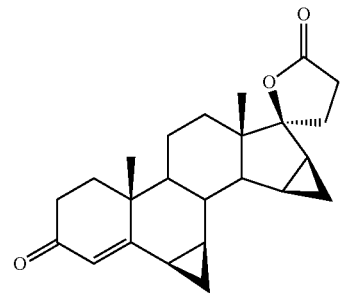

12 Claims, No Drawings

PROCESS FOR THE PREPARATION OF DROSPIRENONE

CROSS-REFERENCE TO RELATED APPLICATIONS

This application is a National Phase of PCT/EP2012/073181, filed 21 Nov. 2012, which claims priority from EP No. 11190133.6, filed 22 Nov. 2011, U.S. Application No. 61/562,626, filed 22 Nov. 2011 and Italian Application No. MI2012A000146, filed 3 Feb. 2012, the specifications of which are all incorporated herein by reference.

FIELD OF THE INVENTION

The present invention relates to a process for the synthesis of drospirenone.

BACKGROUND OF THE INVENTION

The compound of formula 1 below, the chemical name of which is 6β,7β;15β,16β-dimethylene-3-oxo-17α-pregn-4-ene-21,17-carbolactone, is commonly known as drospirenone, also abbreviated as DRSP (abbreviation used in the remainder of the text):

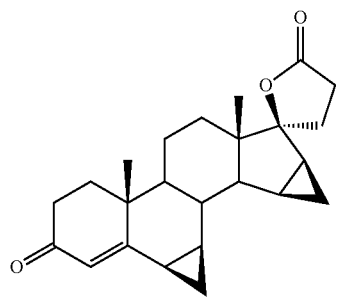

Drospirenone is a synthetic steroid with progestogenic, antimineralocorticoid and antiandrogenic activity; thanks to these characteristics, drospirenone has been used for some time in the preparation of pharmaceutical compositions with contraceptive action for oral administration.

Many processes for the preparation of drospirenone are known in literature.

European patent EP 75189 B1 describes a process which, through various steps commencing from 3β,7α,15α-trihydroxy-5-androsten-17-one, reaches the intermediate 17α-(3-hydroxypropyl)-6β,7β;15β,16β-dimethylene-5β-androstane-3β,5,17β-triol (also simply referred to as "triol" in the remainder of the text), from which the end product drospirenone is obtained by hot oxidation with the pyridine/water/chromium trioxide mixture (Collins reagent). The latter step constitutes the main disadvantage of the process: indeed, like all Cr(VI) compounds, chromium trioxide is a known carcinogen, the use of which is subject to legislative restrictions such that the precautions required during the use and disposal of these products make them virtually unusable. Moreover, the formation of drospirenone in the presence of chromium trioxide generates a series of impurities that reduce the reaction yield, as highlighted in patent EP 918791 B1.

In patent EP 918791 B1 it is disclosed a process that avoids the use of the Collins reagent. In this process, it is employed an oxidant system comprising an oxidizing agent such as sodium bromate and a ruthenium salt as oxidation catalyst; the product of oxidation of the triol is the compound 6β,7β;15β,16β-dimethylene-5β-hydroxy-3-oxo-17α-androstane-21,17-carbolactone, that is generally known in the field with the abbreviation 5β-OH-DRSP (abbreviation that will be used in the following description); this compound is then converted into DRSP by elimination of a water molecule between the positions 4 and 5 of the steroidal skeleton, by means of para-toluenesulfonic acid. This process too envisages the purification of drospirenone by chromatography as in EP 75189 B1. The purity of the raw drospirenone obtained by the method described in EP 918791 B1 is of 93%, a value that is far from acceptable for a pharmaceutical product. The method of EP 918791 B1 thus requires purification by means of chromatography of the crude product downstream the production process. The industrial-scale purification, by means of chromatography, of a product having a market of thousands of kg/year, is however a very significant commitment: a dedicated plant with the use of tons of silica gel, which must then be disposed of and thousands of cubic meters of solvent are required, with a huge economic commitment for the set-up and management logistics of said plant.

The above problem is overcome by the process described in patent EP 1828222 B1, in the name of the Applicant. According to the process of this patent, the crude drospirenone is obtained by the intermediate 17α-(3-hydroxypropyl)-6β,7β;15β,16β-dimethylene-5β-androstane-3β,5,17β-triol, using an hypochlorite of an alkali or alkaline-earth metal (for example calcium hypochlorite) in the presence, as catalyst, of 2,2,6,6-tetramethylpiperidine-1-oxyl radical (known as TEMPO in the field) or derivatives thereof; at the end of this reaction, a mixture of compounds is obtained, containing 5β-OH-DRSP as the main component. An acid (for example para-toluenesulfonic acid) is added to this mixture as dehydrating agent; the drospirenone obtained by this preparation route is brought to pharmaceutical grade by crystallization.

The process of EP 1828222 B1 already resolves many of the problems of the known prior art, but still requires the use of an acid, in particular para-toluenesulfonic acid, in the final phase of synthesis. It is known, from *Tetrahedron Letters* 27(45), 5463-5466, 1986 for example, that drospirenone is unstable to acids: the lactone ring in position 17,21 and the three-membered ring in position 6,7 are not stable in the presence of acids, reacting to give impurities that must therefore be eliminated; this complicates the overall production process of drospirenone and reduces the yields thereof.

Finally, in patent EP 1571153 B1 is disclosed a further possible method for the production of DRSP. Example 11 of this patent describes a process in which: the two carbolactols corresponding to 5β-OH-DRSP, dissolved in methylene chloride, are added to a 5% (by weight) aqueous solution of sodium bicarbonate; calcium hypochlorite, in the presence of TEMPO as catalyst, is added to the biphasic mixture containing the carbolactols; pyridine is then added, and methylene chloride is distilled at room pressure; at the end of the distillation, the reaction mixture is kept hot (that is, at the temperature of methylene chloride distillation), the solvent is distilled under reduced pressure, and the crude reaction product is first chromatographed over silica gel and finally crystallized. Also this procedure suffers from some drawbacks. In first place, it still requires, as most of the previous methods, a final step of chromatography for the isolation of the desired product; chromatography, as discussed below, is undesired in an industrial process, because it prolongs the time of production and entails the use and disposal of huge amounts of solvents and silica. Besides, in the method described in this example, the maximum temperature reached is about 40° C., namely, boiling point of methylene chloride, reached during its distillation at room pressure; this temperature cannot be overcome in this procedure, because at higher temperatures sodium bicarbonate, still present in the mixture, starts to transform into sodium carbonate, with an increase in the pH of the mixture; the higher pH caused by sodium carbonate is capable to open the lactone ring of 5β-OH-DRSP, leading to by-products and in the end to a lower yield in desired product. The relatively low temperatures taught in this example of EP 1571153 B1, however, do not afford satisfactory yields in drospirenone. The yield of drospirenone, calculated starting from 17α-(3-hydroxypropyl)-6β,7β;15β,16β-dimethylene-5β-androstane-3β,5,17β-triol (combined yield of examples 7, production of the carbolactols, and 11, oxidation of the carbolactols) is 62%.

It is therefore an object of the present invention to provide an improved process for the production of drospirenone.

In particular, object of the present invention is to provide a process that avoids the need to use toxic or carcinogenic metals in the oxidation reaction of 17α-(3-hydroxypropyl)-6β,7β;15β,16β-dimethylene-5β-androstane-3β,5,17β-triol as well as the need to use acids in the dehydration of 5β-OH-DRSP that forms the drospirenone, thus allowing an increase in the yield of the end product.

SUMMARY OF THE INVENTION

These objects are achieved with the present invention with a process that comprises the following steps:
  a) oxidation of the compound 17α-(3-hydroxypropyl)-6β,7β;15β,16β-dimethylene-5β-androstane-3β,5,17β-triol with an oxidizing agent in the presence of a catalytic amount of 2,2,6,6-tetramethylpiperidine-1-oxyl radical or a derivative thereof;
  b) removal of the solvent from the reaction mixture by distillation, obtaining a raw oily product containing 6β,7β;15β,16β-dimethylene-5β-hydroxy-3-oxo-17α-androstane-21,17-carbolactone;
  c) addition to said raw oily product of a mixture of water and an organic base and heating of the resulting mixture at a temperature comprised between 45 and 90° C., to form drospirenone.

DETAILED DESCRIPTION OF THE INVENTION

The starting compound of the process of the invention is 17α-(3-hydroxypropyl)-6β,7β;15β,16β-dimethylene-5β-androstane-3β,5,17β-triol. This compound can be prepared according to any known method; preferably, said compound is prepared according to the procedure described in patent EP 1828222 B1 or according to a similar procedure.

The starting compound is then oxidised according to the procedure described in patent EP 1828222 B1, with a suitable oxidising agent in the presence of catalytic amounts of the 2,2,6,6-tetramethylpiperidine-1-oxyl radical or a derivative thereof. Oxidation of the triol could also be achieved according to the procedure described in Italian patent application MI2011A991383 in the name of the Applicant, filed on 25 Jul. 2011, and the contents of which were made public by means of publication in an extended abstract of the application itself at the following web address:
  http://www.chemogroup.com/EN/news/Drospirenone979.pdf
The oxidation procedure of EP 1828222 B1 is however preferred, and the description that follows makes reference to the method of said patent.

With "suitable oxidising agent" it is meant a compound selected among the hypohalides of alkali and alkaline-earth metals, iodine, oxygen in the presence of CuCl, potassium peroxymonosulphate ($KHSO_5$), known commercially as Oxone®, and 1,3,5-trichloro-2,4,6-triazinetrione; the preferred oxidising agents are calcium or sodium hypochlorite. The oxidising agent is employed in an amount, measured in equivalents, at least equal to 3 times the number of moles of the triol to be oxidised, and preferably at least equal to 3.3 times the moles of said triol.

The catalyst employed is selected among the 2,2,6,6-tetramethylpiperidine-1-oxyl radical, known as TEMPO, or derivatives thereof, such as the 4-hydroxy-2,2,6,6-tetramethylpiperidine-1-oxyl radical, the 4-methoxy-2,2,6,6-tetramethyl piperidine-1-oxyl radical, the 4-benzoyloxy-2,2,6,6-tetramethylpiperidine-1-oxyl radical, the 4-acetamido-2,2,6,6-tetramethylpiperidine-1-oxyl radical, the 4-amino-2,2,6,6-tetramethylpiperidine-1-oxyl radical, the 4-carboxy-2,2,6,6-tetramethylpiperidine-1-oxyl radical, the 4-cyano-2,2,6,6-tetramethylpiperidine-1-oxyl radical, and the 4-oxo-2,2,6,6-tetramethylpiperidine-1-oxyl radical.

The catalyst is preferably employed in a molar amount comprised between about 5 and 15% of the moles of the triol to be oxidised; the inventors have observed that with molar amounts below 5% the reaction only takes place with limited yields, while molar amounts above 15% do not result in increased yield and would therefore constitute a waste of catalyst.

The reaction is carried out in an organic solvent chosen among acetone, ethers, such as for example methyl tert-butyl ether and tetrahydrofuran, esters such as for example ethyl acetate, hydrocarbons such as for example toluene, halogenated hydrocarbons such as methylene chloride and mixtures of these solvents, at a temperature comprised between 0 and 40° C., preferably between 10 and 30° C.

Preferred conditions for the oxidation reaction are the use of calcium hypochlorite in a mixture of methylene chloride/tetrahydrofuran (preferably in a volume ratio of at least 10/1) as solvent, at a temperature comprised between 20 and 30° C., in the presence of TEMPO radical between about 10% and 14% in moles (with respect to the triol) and in the presence of an aqueous solution of sodium bicarbonate.

The mixture obtained at the end of the oxidation reaction is subjected to the usual treatments for the recovery of an organic compound from an organic mixture, such as washing with water-based solutions and filtering, and lastly to distillation to remove the solvent.

On completion of the distillation, an oily product is obtained, which is not further purified. This product is an oily mixture containing mainly the compound 6β,7β;15β,16β-dimethylene-5β-hydroxy-3-oxo-17α-androstane-21,17-carbolactone, that is not isolated. To this oily mixture a mixture of water/organic base is directly added. Bases that can be used are pyridine, triethylamine, a collidine (any one of the possible trimethylpyridines), 1,8-diazabicyclo[5.4.0]undec-7-ene and 1,5-diazabicyclo[4.3.0]non-5-ene and derivatives thereof. The preferred base is pyridine. Pyridine is a reagent/solvent commonly employed in industry; it has a low cost, is stable over time and does not pose particular problems of application, and the water/pyridine mixture can be recovered at the end of the reaction by means of simple distillation and re-used in successive production cycles.

The volume ratio of water to the base can vary between about 5:1 and 1:4. In the case of pyridine, for example, it is possible to use the azeotropic mixture, which presents a water/pyridine volume ratio of 0.74. The inventors have observed that it is not necessary for the water used to be purified or distilled.

The reaction temperature can vary generally between 45 and 90° C., depending on the base used and on its volume ratio to water: the water/base mixtures prepared with the aforementioned bases have boiling temperatures that vary depending on the actual composition, and the maximum temperature of the reaction must be below the boiling temperature of the specific water/base mixture used.

The reaction is completed in a time period comprised between 1 and 20 hours, and does not need to be carried out in an inert atmosphere.

The crude drospirenone produced with the described process has an HPLC purity grade above 98.5%; further purifications of the product, aimed at obtaining a pharmaceutical grade thereof, can be achieved according to the common techniques known to industry experts, such as recrystallization.

Thanks to the use of a mixture of reagents that present no danger, safety and flammability problems, the reaction can be carried out in a simple plant, created without special safety restrictions, and which does not require specific heating or cooling systems. On completion of the reaction there are no residues containing heavy metals or other hazardous waste.

The invention will be further illustrated by means of the following examples.

In the examples, the indicated amounts of drospirenone obtained are measured by means of quantitative analyses carried out on the raw product (HPLC titration vs. reference sample; HPLC instrument Agilent model 1200); the yields are calculated on the basis of these absolute amounts.

EXAMPLE 1

28 g of 17α-(3-hydroxypropyl)-6β,7β;15β,16β-dimethylene-5β-androstane-3β,5,17β-triol are dissolved in the reaction vessel at 35° C. in 56 ml of tetrahydrofuran. 712 ml of chloromethane and 420 ml of 10% by weight aqueous solution of sodium bicarbonate are added and the biphasic mixture thus obtained is cooled under agitation at 10° C.

The TEMPO catalyst and calcium hypochlorite as oxidising agent are added in successive doses under agitation, leaving the mixture to react for 1 hour after each addition and monitoring the degree of progress of the reaction with thin layer chromatography (TLC) at the end of each period. In particular, 700 mg of TEMPO are added in the first dosage and 11.2 g of calcium hypochlorite are added a few minutes later.

It is agitated while bringing the temperature to 28-30° C. After 1 hr the TLC check shows a partial reaction. While maintaining agitation at a temperature of 28-30° C., a second dosage of 500 mg of TEMPO takes place and 11.2 g of calcium hypochlorite are added a few minutes later. The reaction is left to progress and after one hour an incomplete reaction is still observed with TLC. While continuing to maintain agitation at 28-30° C., a third dosage of 140 mg of TEMPO takes place and 4.2 g of calcium hypochlorite are added a few minutes later. One hour later the TLC check confirms that the reaction is complete, the starting triol not being detectable.

110 ml of dichloromethane are added to the reaction mixture that is filtered with diatomaceous earth. The filter is washed with further 100 ml of dichloromethane. The aqueous and organic phases are separated and the latter is successively washed with 520 ml of 2% by weight aqueous $NaHSO_4$ solution and with 520 ml of 4% by weight aqueous sodium chloride solution. The pH of the final aqueous phase is 7. The organic phase is agitated for a few minutes with 1.2 g of decolorizing charcoal and with 1.2 g or diatomaceous earth. The suspension is filtered, washing the filter with 60 ml of dichloromethane.

The organic phase is distilled until an oily, semi-solid residue is obtained that is not removed from the reaction vessel. 280 ml of water and 280 ml of pyridine are added to the same vessel. The mixture is brought, under agitation, to a temperature of 45-50° C. for 16 hours. After this period, a TLC check confirms that the reaction is complete; a homogeneous spot is observed with Rf corresponding to the DRSP (controlled with a spot of pure product in the TLC itself).

310 ml of pyridine-water mixture are distilled under reduced pressure (T of the distillation vapours=24-25° C.). 460 ml of water are added and the distillation then takes place, removing further 50 ml of solvent. 75 ml of isopropyl acetate are added and the system is agitated while cooling with a water-ice bath, observing in the distillation flask the formation of a solid that is filtered and dried under reduced pressure. 12.3 g of drospirenone are obtained. A further 6.1 g of drospirenone are obtained from concentration of the organic phase, with total yield of the recovered product, relating to the starting triol, equal to 70%.

EXAMPLE 2

The oxidation reaction of Example 1 is repeated, using 1 g of the starting triol; reagents and solvents are used in the same proportions, relative to the triol, as in Example 1.

At the end of the oxidation phase 10 ml of water and 20 ml of pyridine are added to the same vessel and the mixture is heated under agitation to a temperature comprised between 58 and 62° C. for 7 hours. At the end of this period, the TLC check confirms that the reaction is complete (homogeneous spot with Rf corresponding to drospirenone).

The reaction mixture is distilled under reduced pressure thus obtaining 1023 mg of crude product which, titrated by HPLC, contain 685 mg of drospirenone, with a reaction yield, calculated with respect to the initial triol, of 73%.

EXAMPLE 3

The procedure of Example 2 is repeated, in this case adding 10 ml of water and 15 ml of pyridine at the end of the oxidation reaction. After the TLC check, which confirms that the reaction is complete (homogeneous spot with Rf corresponding to drospirenone), the reaction mixture is distilled under reduced pressure, thus obtaining 1027 mg of crude product which, titrated by HPLC, contain 684 mg of drospirenone, with a reaction yield, calculated with respect to the initial triol, of 73%.

EXAMPLE 4

The procedure of Example 2 is repeated, in this case adding 10 ml of water and 10 ml of pyridine at the end of the oxidation reaction. After the TLC check, which confirms that the reaction is complete (homogeneous spot with Rf corresponding to drospirenone), the reaction mixture is distilled under reduced pressure, thus obtaining 1,005 mg of crude product which, titrated by HPLC, contain 679 mg of drospirenone, with a reaction yield, calculated with respect to the initial triol, of 72%.

EXAMPLE 5

The procedure of Example 2 is repeated, in this case adding 10 ml of water and 5 ml of pyridine at the end of the oxidation reaction. After the TLC check, which confirms that the reaction is complete (homogeneous spot with Rf corresponding to drospirenone), the reaction mixture is distilled under reduced pressure, thus obtaining 995 mg of crude product which, titrated by HPLC, contain 652 mg of drospirenone, with a reaction yield, calculated with respect to the initial triol, of 69%.

EXAMPLE 6

The procedure of Example 2 is repeated, in this case adding 10 ml of water and 2.5 ml of pyridine at the end of the oxidation reaction, while continuing to heat the mixture, in this case for 15 hours. After the TLC check, which confirms that the reaction is complete (homogeneous spot with Rf corresponding to drospirenone), the reaction mixture is distilled under reduced pressure, thus obtaining 1,012 mg of crude product which, titrated by HPLC, contain 579 mg of drospirenone, with a reaction yield, calculated with respect to the initial triol, of 62%.

EXAMPLE 7

Comparative

The procedure of Example 2 is repeated, in this case adding 10 ml of water and 10 ml of pyridine at the end of the oxidation reaction, while in this case continuing to heat the mixture to a temperature comprised between 38 and 42° C. for 20 hours, that is, below the lower limit of the range of temperatures of the invention for the dehydration reaction. After the TLC check, which confirms that the reaction is complete (homogeneous spot with Rf corresponding to drospirenone), the reaction mixture is distilled under reduced pressure, thus obtaining 895 mg of crude product which, titrated by HPLC, contain 329 mg of drospirenone with a reaction yield, calculated with respect to the initial triol, of 35%.

EXAMPLE 8

The procedure of Example 7 is repeated, heating in this case the mixture to a temperature comprised between 78 and 82° C. for 15 hours. After the TLC check, which confirms that the reaction is complete (homogeneous spot with Rf corresponding to drospirenone), the reaction mixture is distilled under reduced pressure, thus obtaining 1,002 mg of crude product which, titrated by HPLC, contain 652 mg of drospirenone with a reaction yield, calculated with respect to the initial triol, of 69%.

EXAMPLE 9

Comparative

The oxidation reaction of Example 2 is repeated.
On completion, 20 ml of pyridine are added to the oxidation product (without water). The mixture is heated under agitation for 18 hours at a temperature comprised between 48 and 52° C.
At the TLC check, the reaction is largely incomplete: the TLC shows two main spots, the principal one corresponding to the initial triol and the secondary spot to drospirenone. The solvent is recovered while recovering 1027 mg of residue that presents the same TLC profile as the previous check. Evaluations of yield are not carried out on the product.

EXAMPLE 10

Comparative

The oxidation reaction of Example 1 is repeated, using 500 mg of the initial triol; reagents and solvents are used in the same proportions, relative to the triol, as in Example 1.
At the end of the oxidation phase, 5 ml of ethanol, and 50 mg of sodium methylate ($CH_3ONa$) are added to the reaction flask and the mixture is kept under agitation for 1 hr at a temperature comprised between 38 and 42° C. At the end of this period, the TLC check confirms that the reaction is complete (homogeneous spot with Rf corresponding to drospirenone). The reaction solution pH is corrected to ≈6 with acetic acid then the solvent is distilled under reduced pressure.
The residue is re-dissolved with 5 ml of water and 5 ml of dichloromethane. The organic phase is dry concentrated under reduced pressure.
The product obtained (395 mg), re-checked by TLC, shows more than one spot. The content in drospirenone in the sample, determined by HPLC analysis with a reference sample, is equal to 36% by weight.
The reaction yield, calculated with respect to the initial triol, is of 30%.

EXAMPLE 11

The oxidation reaction of Example 1 is repeated, preparing an initial mixture with 28 g of triol dissolved in 60 ml of tetrahydrofuran at 35° C., to which 710 ml of dichloromethane and 420 ml of an aqueous solution of sodium bicarbonate at 10% are added, thus obtaining a biphasic mixture which is cooled to 10° C. under agitation.
The addition of calcium hypochlorite and TEMPO takes place in three successive dosages, as described in Example 1, under agitation and while maintaining the reacting mixture at a temperature of 28-30° C.; 700 mg of TEMPO are added in the first dosage and 11.2 g of calcium hypochlorite are added a few minutes later (TLC check result after 1 hour: partial reaction); 510 mg of TEMPO are added in the second dosage and 11.4 g of calcium chloride are added a few minutes later (TLC check result after 1 hour: partial reaction); and 130 mg of TEMPO are added in the third dosage and 4.0 g of calcium hypochlorite are added a few minutes later. One hour after this last dosage of oxidising agent and catalyst, the reaction is complete, the starting triol not being detected at the TLC check.
120 ml of dichloromethane are added to the reaction mixture that is filtered with diatomaceous earth. The filter is washed with further 100 ml of dichloromethane.
The phases are separated and the organic phase is successively washed with 520 ml of 2% by weight aqueous $NaHSO_4$ solution and then with 520 ml of 4% by weight aqueous sodium chloride solution. The pH of the final aqueous phase is 7.
The organic phase is agitated for a few minutes with 1.2 g of decolorizing charcoal and with 1.5 g or diatomaceous earth. The suspension is filtered, washing the filter with 60 ml of dichloromethane.
The organic phase is roughly distilled until an oily, semisolid residue is obtained. 280 ml of water and 140 ml of pyridine are added to the distillation flask. The mixture is heated under agitation to a temperature comprised between 58 and 62° C. for 20 hours. At the end of this period, a TLC check confirms that the reaction is complete: a homogeneous spot with Rf corresponding to drospirenone is observed. 200 ml of pyridine/water mixture are distilled under reduced pressure (temperature of the distillation vapours=24-25° C.).

200 ml of water are added, the system is cooled to 20-25° C. and extracted with 300 ml of dichloromethane. After washing with water, the organic phase is filtered and treated with decolorizing charcoal (1.2 g), diatomaceous earth (1.2 g), sodium sulphate (4.8 g) and refiltered The solvent is distilled, eliminating the residual pyridine by means of distillation with methyl isobutyl ketone.

The residue, crystallized by isopropyl acetate, provides 14.5 g of drospirenone (constant weight after drying at 50° C. and reduced pressure). A further 4.36 g of drospirenone are recovered by further crystallization from the mother liquors. The crystallization residue, checked in TLC, shows the presence of drospirenone. Following chromatography, a further 1.4 g of drospirenone are recovered, for a total recovered product yield, relating to the initial triol, of 78%.

EXAMPLE 12

The oxidation reaction of Example 1 is repeated, using 500 mg of the initial triol; reagents and solvents are used in the same proportions, relative to the triol, as in Example 1.

At the end of the oxidation phase, 5 ml of water and 15 ml of pyridine are added to the reaction flask and the mixture is heated under agitation at a temperature comprised between 48 and 52° C. for 15 hours. At the end of this period, the TLC check confirms that the reaction is complete, showing a homogeneous spot with Rf corresponding to drospirenone.

The reaction mixture is distilled under reduced pressure thus obtaining 502 mg of crude product. The content in drospirenone in the sample, always determined by HPLC analysis against the reference sample, turns out of 66% (by weight) for a total amount of 331 mg of DRSP, corresponding to a reaction yield, relating to the initial triol, of 71%.

EXAMPLE 13

Comparative

The oxidation reaction of Example 12 is repeated.

At the end of the oxidation phase, 20 ml of water are added to the reaction flask; a suspension is formed. The mixture is heated for 16 hours under agitation at a temperature comprised between 48 and 52° C.

After this period, the TLC check reveals that the reaction is highly incomplete: the TLC shows two spots, with the secondary, barely visible spot, corresponding to drospirenone (traces).

EXAMPLE 14

Comparative

The oxidation reaction of Example 2 is repeated; reagents and solvents are used in the same proportions, relative to the triol, as in Example 1.

At the end of the oxidation phase, and after distillation, 100 mg of KOH are added to the reaction vessel.

The mixture is heated under agitation to a temperature comprised between 58 and 62° C. for 16 hours. The formation of drospirenone is not observed at the TLC check. In confirmation of the TLC result, the reaction mixture is analysed by HPLC, giving as result an HPLC titre in drospirenone equal to 1.0%.

EXAMPLE 15

Comparative

The oxidation reaction of Example 15 is repeated.

At the end of the oxidation phase, and after distillation, 10 ml of 1.8-diazabicyclo[5.4.0]undec-7-ene (DBU) are added to the reaction vessel.

The mixture is heated under agitation to a temperature comprised between 58 and 62° C. for 16 hours. A partial reaction is observed at TLC check, with principal spot not corresponding to drospirenone and with Rf=0. The organic solution is titrated with HPLC thus obtaining a molar reaction yield of 34%.

EXAMPLE 16

Comparative

The oxidation reaction of Example 15 is repeated.

At the end of the oxidation phase, and after distillation, 10 ml of triethylamine (TEA) are added to the reaction vessel.

The mixture is heated under agitation to a temperature comprised between 58 and 62° C. for 16 hours. The formation of drospirenone is not observed at the TLC check. In confirmation of the TLC result, the reaction mixture is analysed by HPLC, giving as result an HPLC titre in drospirenone equal to 2.1%.

Comment to the Results

The results of the tests are summarized in the table below, which reports, in the columns from left to right: the number of the Example (the asterisk indicates a comparative example), the millimoles of starting triol, the volume/volume ratio of water to the base (when no ratio is indicated, in comparative examples, it is given the indication of the base used, or water only in comparative example 13), the temperature and time conditions of the dehydration reaction, the millimoles of drospirenone obtained, and the yield of drospirenone obtained (as percent relative to the moles of starting triol).

| Ex. | mmol triol | H$_2$O/base ratio (v/v) | Dehydration conditions | | DRSP | |
|---|---|---|---|---|---|---|
| | | | temperature (° C.) | time (hours) | mmol DRSP | yield (%) |
| 1 | 71.69 | 1:1 | 45-50 | 16 | 50.20 | 70 |
| 2 | 2.56 | 1:2 | 58-62 | 7 | 1.87 | 73 |
| 3 | 2.56 | 1:1.5 | 58-62 | 7 | 1.87 | 73 |
| 4 | 2.56 | 1:1 | 58-62 | 7 | 1.85 | 72 |
| 5 | 2.56 | 2:1 | 58-62 | 7 | 1.78 | 69 |
| 6 | 2.56 | 4:1 | 58-62 | 15 | 1.58 | 62 |
| 7* | 2.56 | 1:1 | 38-42 | 20 | 0.90 | 35 |
| 8 | 2.56 | 1:1 | 78-82 | 15 | 1.78 | 69 |
| 9* | 2.56 | pyridine only | 48-52 | 18 | n.a. | n.a. |
| 10* | 1.28 | CH$_3$ONa in EtOH | 38-42 | 1 | n.a. | 30 |
| 11 | 71.69 | 2:1 | 58-62 | 20 | 55.28 | 77 |
| 12 | 1.28 | 1:3 | 48-52 | 15 | 0.90 | 71 |
| 13* | 1.28 | water only | 48-52 | 16 | n.a. | traces |
| 14* | 2.56 | KOH | 58-62 | 16 | n.a. | 1 |
| 15* | 2.56 | DBU | 58-62 | 16 | n.a. | 34 |
| 16* | 2.56 | TEA | 58-62 | 16 | n.a. | 2 |

As can be seen by the comparison of results between comparative example 7 on one hand, and examples 1, 4 and 8 on the other hand, simply reducing the temperature a few degrees below 45° C., the lower limit of the range of the invention for the dehydration reaction, leads to a dramatic reduction in yield of DRSP, that goes down to about one half compared to the figures obtained with the process according to the invention.

Similarly, the examples show poor or negligible DRSP yields if another condition of the invention, namely the use of a mixture of an organic base with water as dehydrating agent, is not adopted. As can be observed from examples 9, 10, and 14-16, the use of bases, even strong ones (such as CH$_3$ONa in comparative example 10) is not efficient if these are not used in mixture with water.

Finally, comparative example 13 confirms that heating alone (treatment with water alone at about 50° C. for 16 hours) is not effective to obtain dehydration of 5β-OH-DRSP.

The invention claimed is:

1. Process for the preparation of drospirenone comprising the following steps:
   a) oxidation of the compound 17α-(3-hydroxypropyl)-6β,7β;15β,16β-dimethylene-5β-androstane-3β,5,17β-triol with an oxidizing agent in the presence of a catalytic amount of; a catalyst selected from the group consisting of the 2,2,6,6-tetramethylpiperidine-1-oxyl radical, the 4-hydroxy-2,2,6,6-tetramethylpiperidine-1-oxyl radical, the 4-methoxy-2,2,6,6-tetramethylpiperidine-1-oxyl radical, the 4-benzoyloxy-2,2,6,6-tetramethylpiperidine-1-oxyl radical, the 4-acetamido-2,2,6,6-tetramethylpiperidine-1-oxyl radical, the 4-amino-2,2,6,6-tetramethylpiperidine-1-oxyl radical, the 4-carboxy-2,2,6,6-tetramethylpiperidine-1-oxyl radical, the 4-cyano-2,2,6,6-tetramethylpiperidine-1-oxyl radical, and the 4-oxo-2,2,6,6-tetramethylpiperidine-1-oxyl radical;
   b) removal of the solvent from the reaction mixture by distillation, obtaining a raw oily product containing 6β,7β;15β,16β-dimethylene-5β-hydroxy-3-oxo-17α-androstane-21,17-carbolactone; and
   c) addition to said raw oily product of a mixture of water and an organic base and heating of the resulting mixture at a temperature comprised between 45 and 90° C., to form drospirenone.

2. The process according to claim 1, wherein steps a), b) and c) take place in a single reaction container, with no isolation and purification of intermediate compounds.

3. The process according to claim 1, wherein the oxidizing agent is selected from the group consisting of hypohalides of alkali and alkaline-earth metals, iodine, oxygen in the presence of CuCl, potassium peroxymonosulfate (KHSO$_5$), and 1,3,5-trichloro-2,4,6-triazinetrione.

4. The process according to claim 3, wherein said oxidizing agent is selected from the group consisting of calcium hypochlorite and sodium hypochlorite.

5. The process according to claim 4, wherein the oxidizing agent is employed in an amount, measured in equivalents, at least equal to 3 times the number of moles of 17α-(3-hydroxypropyl)-6β,7β;15β,16β-dimethylene-5β-androstane-3β,5,17β-triol.

6. The process according to claim 5, wherein said oxidizing agent is employed in an amount, measured in equivalents, at least equal to 3.3 times the number of moles of 17α-(3-hydroxypropyl)-6β,7β;15β,16β-dimethylene-5β-androstane-3β,5,17β-triol.

7. The process according to claim 1, wherein the catalyst is employed in a molar amount comprised between about 5% and 15% of the moles of 17α-(3-hydroxypropyl)-6β,7β;15β,16β-dimethylene-5β-androstane-3β,5,17β-triol.

8. The process according to claim 1, wherein the oxidation reaction of step a) is carried out in an organic solvent selected from the group consisting of acetone, ethers, esters, hydrocarbons, halogenated hydrocarbons and mixtures thereof, at a temperature comprised between 0 and 40° C.

9. The process according to claim 8, wherein said oxidation step a) is carried out with calcium hypochlorite as the oxidizing agent, a mixture of methylene chloride/tetrahydrofuran as the solvent, at a temperature comprised between 20 and 30° C. in the presence of 2,2,6,6-tetramethylpiperidine-1-oxyl radical as the catalyst and in the presence of an aqueous sodium bicarbonate solution.

10. The process according to in which claim 1, wherein the base used in mixture with water in the dehydration step c) is selected from the group consisting of pyridine, triethylamine, a collidine, 1,8-diazabicyclo[5.4.0]undec-7-ene and 1,5-diazabicyclo[4.3.0]non-5-ene and derivatives thereof, and the volume ratio between water and the base is comprised between about 5:1 and 1:4.

11. The process according to claim 10, wherein said base is pyridine.

12. The process according to claim 1, wherein the dehydration step c) lasts between 1 and 20 hours.

* * * * *